US00PP09927P

United States Patent [19]

Fuess

[11] Patent Number: Plant 9,927

[45] Date of Patent: Jun. 17, 1997

[54] CHRYSANTHEMUM PLANT NAMED 'EMPIRE CABERNET'

[76] Inventor: Janet S. Fuess, 22 Country Club Dr., New York Mills, N.Y. 13417

[21] Appl. No.: 670,279

[22] Filed: Jun. 13, 1996

[51] Int. Cl.[6] ..... A01H 5/00

[52] U.S. Cl. ..... Plt./76

[58] Field of Search ..... Plt./76, 82

[56] References Cited

U.S. PATENT DOCUMENTS

P.P. 2,023 2/1961 Dunham ..... Plt./76

P.P. 8,782 6/1994 Fuess ..... Plt./76

*Primary Examiner*—Howard J. Locker

*Attorney, Agent, or Firm*—Foley & Lardner

[57] ABSTRACT

A new and distinct cultivar of Chrysanthemum plant named Empire Cabernet, characterized particularly by its red-purple ray florets, with the ray florets around the edges fading upon maturity to a much lighter red-purple color; fully double flowers which have no disc florets and which are very resistant to shattering; semi-upright cushion habit; 6.0–6.5 cm capitulum diameter; a natural season flower date of September 22, in New Hartford, N.Y. and seven week flower response in light/shade programs.

1 Drawing Sheet

The present invention comprises a new and distinct cultivar of Chrysanthemum, botanically known as *Dendranthema grandiflora*, and referred to by the cultivar name Empire Cabernet.

Empire Cabernet is a product of a planned breeding program which had the objective of creating new Chrysanthemum cultivars with large decorative capitulum type, purple ray floret color, freely branching habit, and suitability for production as a garden variety. Such traits in combination were not present in previously available commercial cultivars.

Empire Cabernet was originated from a hybridization made by the inventor Janet S. Fuess in a controlled breeding program in New Hartford, N.Y. in 1991. The female parent was Pink Champagne, disclosed in U.S. Plant Pat. No. 6,920. The male parent of Empire Cabernet was a pink decorative seedling identified as B88-2, a proprietary breeding line.

Empire Cabernet was discovered and selected by the inventor as one flowering plant within the progeny of the stated parentage in September 1992 in a controlled environment in new Hartford, N.Y.

The first act of asexual reproduction of Empire Cabernet was accomplished when vegetative cuttings were taken by the inventor from the initial selection in October 1992 in a controlled environment in New Hartford, N.Y. Horticultural examination of selected units initiated in September 1993 has demonstrated that the combination of characteristics as herein disclosed for Empire Cabernet are firmly fixed and are retained through successive generations of asexual reproduction.

Empire Cabernet has not been observed under all possible environmental conditions. The phenotype may vary significantly with variations in environment such as temperature, light intensity, and day length, without, however, any variation in genotype. The following observations, measurements and comparisons describe plants grown in New Hartford, N.Y. under natural outdoor conditions which approximate those generally used in commercial practice.

The following traits have been repeatedly observed and are determined to be basic characteristics of Empire Cabernet, which in combination distinguish this Chrysanthemum as a new and distinct cultivar:

1. A pleasing red-purple ray floret color, which fades around the edges of the flower as the flower matures to a much lighter red-purple. this provides an interesting bicolor effect for maturing flowers.

2. Capitulum 6.0–6.5 cm in diameter.
3. Average of 378 ray florets per flower.
4. Fully double flowers, with no disc florets.
5. Fully expanded ray florets approximately 2.9 cm long and 0.8 cm wide.
6. Flowers very resistant to shattering.
7. Seven week flower response in light/shade programs.
8. A natural season flowering date of September 22 in New Hartford, N.Y.
9. Semi-upright cushion habit.

Of the many commercial cultivars known to the present inventor, the most similar in comparison to Empire Cabernet is Empire Chablis, disclosed in U.S. Plant Pat. No. 8,986.

In comparison to Empire Chablis, Empire Cabernet has a completely different ray color (purple compared to white), and flowers approximately 3½ weeks later in natural season. The semi-upright habit, capitulum size and texture, and overall plant height are similar to those same characteristics of Empire Chablis.

The accompanying color photographic drawing comprises a top perspective view showing typical flower and foliage characteristics of Empire Cabernet, with colors being as nearly true as possible with illustrations of this type.

In the following description, color references are made to The Royal Horticultural Society Colour Chart. The color values were determined between 2:00 PM and 4:00 PM on Oct. 8, 1995 under 4,000 foot candles at New Hartford, N.Y.

Classification:

*Botanical.*—*Dendranthema grandiflora* cv. Empire Cabernet.

*Commercial.*—Decorative garden mum.

INFLORESCENCE:

A. Capitulum:

*Form.*—Flat decorative.

*Type.*—Almost fully double.

*Diameter across face.*—6.0–7.0 cm.

B. Corolla of ray florets:

*Color (General tonality from a distance of three meters).*—Red-purple.

*Color (upper surface).*—63A, with edges upper maturity fading to 63D as flower matures.

*Color (under surface).*—65D.

C. Corolla of disc florets: No disc florets.

D. Reproductive organs:

*Androecium.*—None.

*Gynoecium.*—Present on ray florets; style 0.6 cm, bifurcated.

PLANT

A. General appearance:

*Height.*—25–35 cm, when grown in an 8" pot.

*Form.*—Semi-upright cushion habit.

B. Foliage:

*Color (upper surface).*—137A.

*Color (lower surface).*—137C.

*Size and shape.*—6.0–7.0 cm long, 3.5–4.0 cm wide, 5-lobed.

It is claimed:

1. A new and distinct cultivar of Chrysanthemum plant named Empire Cabernet, as illustrated and described.

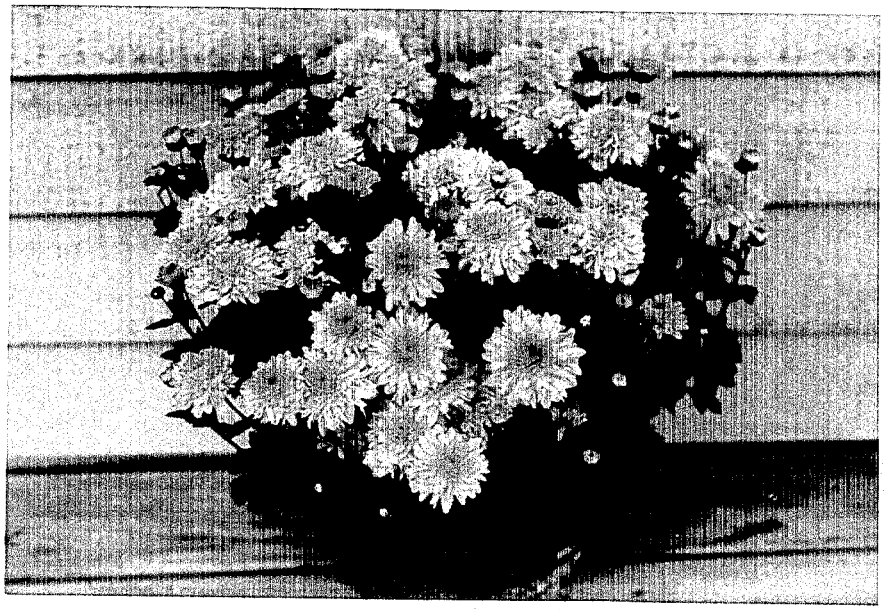

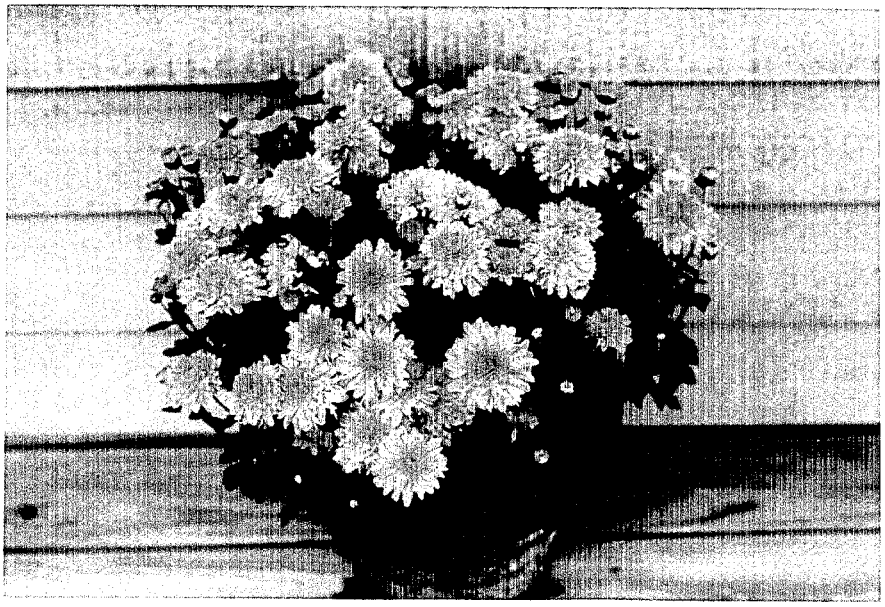

* * * * *